US009014781B2

(12) United States Patent
Tan et al.

(10) Patent No.: US 9,014,781 B2
(45) Date of Patent: Apr. 21, 2015

(54) SYSTEMS AND METHODS FOR MAGNETIC RESONANCE ANGIOGRAPHY

(75) Inventors: Ek Tsoon Tan, Mechanicsville, NY (US); Thomas Kwok-Fah Foo, Clifton Park, NY (US); Vincent B. Ho, N. Bethesda, MD (US)

(73) Assignee: General Electric Company, Niskayuna, NY (US)

( * ) Notice: Subject to any disclaimer, the term of this patent is extended or adjusted under 35 U.S.C. 154(b) by 466 days.

(21) Appl. No.: 13/451,178

(22) Filed: Apr. 19, 2012

(65) Prior Publication Data
US 2013/0281829 A1 Oct. 24, 2013

(51) Int. Cl.
A61B 5/055 (2006.01)
A61B 5/026 (2006.01)

(52) U.S. Cl.
CPC .............. *A61B 5/055* (2013.01); *A61B 5/0263* (2013.01)

(58) Field of Classification Search
USPC ................................................ 600/410, 420
See application file for complete search history.

(56) References Cited

U.S. PATENT DOCUMENTS

| 6,031,374 | A | 2/2000 | Epstein et al. |
| 6,192,264 | B1 | 2/2001 | Foo et al. |
| 6,236,738 | B1 | 5/2001 | Zhu et al. |
| 6,639,211 | B1 | 10/2003 | Anand et al. |
| 2004/0073105 | A1 | 4/2004 | Hamilton et al. |
| 2004/0113613 | A1 | 6/2004 | Markl et al. |
| 2008/0015428 | A1 | 1/2008 | Epstein et al. |
| 2009/0256568 | A1 | 10/2009 | Wiesinger et al. |

FOREIGN PATENT DOCUMENTS

EP 0488496 B1 3/1999

OTHER PUBLICATIONS

Hossain, M.I., et al., "Magnetic Resonance Angiography—An Advanced Technique in MRI Using Flow Imaging", Signal Processing Algorithms, Architectures, Arrangements and Applications, 2007, Issue Date: Sep. 7-7, 2007, on pp. 109-114, E-ISBN: 978-1-4244-1515-1, Print ISBN: 978-1-4244-1514-4, References Cited: 15.

*Primary Examiner* — Peter Luong
(74) *Attorney, Agent, or Firm* — Melissa K. Dobson

(57) ABSTRACT

Systems and methods for Magnetic Resonance Angiography (MRI) are provided. One method includes obtaining Magnetic Resonance (MR) velocity data and determining a distance map for one or more vessels to define a distance path. The method also includes calculating, using the MR velocity data, at a plurality of time intervals and for a plurality of pixels (i) a distance traveled during a current time interval as a current distance traveled, wherein a total distance traveled is incremented by the current distance traveled and (ii) a bolus signal using a bolus signal profile, the distance path and total distance traveled, wherein a current time interval is incremented by a defined time step.

24 Claims, 7 Drawing Sheets

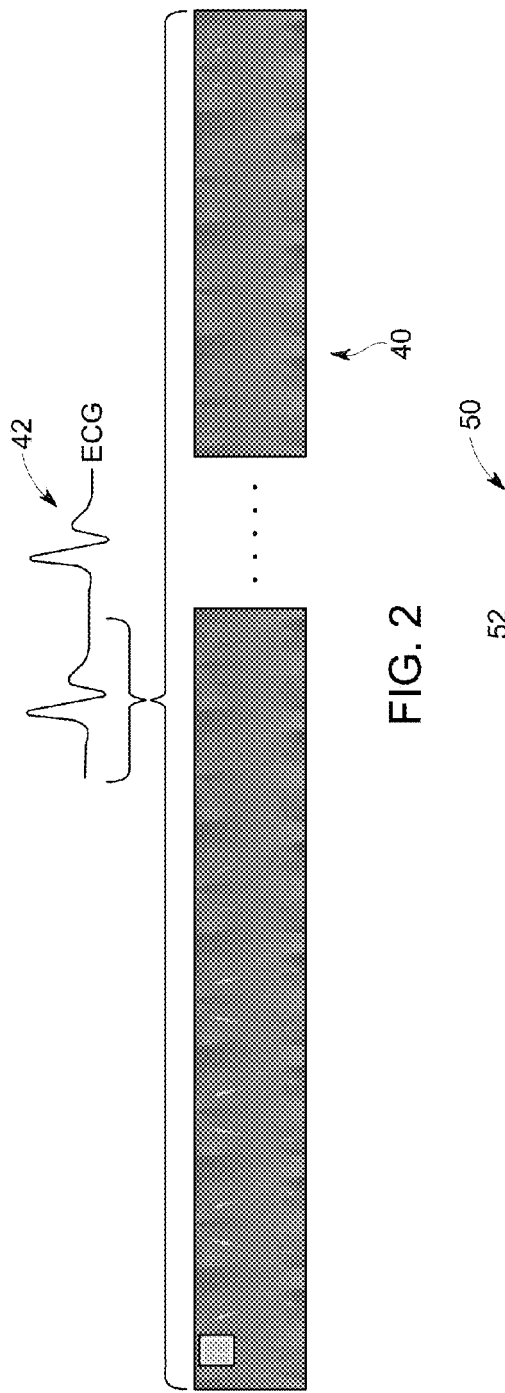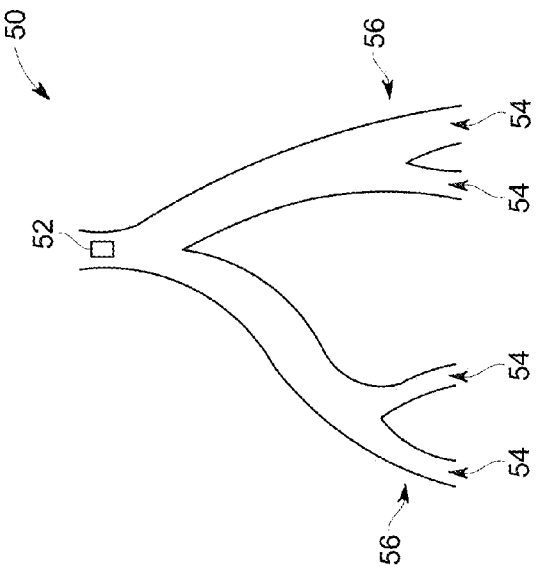
FIG. 2
FIG. 3

SYSTEMS AND METHODS FOR MAGNETIC RESONANCE ANGIOGRAPHY

BACKGROUND

Magnetic Resonance Angiography (MRA) uses Magnetic Resonance Imaging (MRI) to image blood vessels. For example, MRA may be used to generate images of arteries in order to detect different conditions, such as stenosis, occlusions or aneurysms. MRA may be used to image arteries in different regions of a patient, including the head and neck arteries, the thoracic or abdominal aorta, the renal arteries, and the peripheral arteries, to depict the vascular anatomy or to provide functional information regarding blood flow. MRA can also be used to generate images of the veins which typically run in parallel, but with blood flow in the opposite direction to arteries.

There are different methods for generating MRA images. For example, contrast enhanced MRA (CE-MRA) includes injecting contrast agents into a patient and imaging the contrast agent as the contrast agent passes through the arteries or veins of the patient. However, in CE-MRA, timing is important such that any timing problems can result in a degradation of image quality. Additionally, the exogenous contrast agent may pose a contraindication for patients with renal functional impairments because of the poor clearance of the contrast agent from the body. One such risk was identified with chelates of Gadolinium used as a contrast agent where a patient with severely compromised renal function exhibited symptoms of Nephrogenic Systemic Fibrosis (NSF).

Phase-contrast MRA (PC-MRA) is also known and used to encode the velocity of moving blood (of both arteries and veins) in the phase component of the MR signals. However, PC-MRA often has a limited image field-of-view and, when triggered using electro-cardiogram (ECG) signals, provides aggregate blood flow velocity information averaged for a single cardiac cycle.

BRIEF DESCRIPTION

In accordance with various embodiments, a non-transitory computer readable storage medium for Magnetic Resonance Angiography (MRA) using a processor is provided. The non-transitory computer readable storage medium includes instructions to command the processor to obtain Magnetic Resonance (MR) velocity data and determine a distance map for one or more vessels to define a distance path. The non-transitory computer readable storage medium also includes instructions to command the processor to calculate, using the MR velocity data, at a plurality of time intervals and for a plurality of pixels (i) a distance traveled during a current time interval as a current distance traveled, wherein a total distance traveled is incremented by the current distance traveled and (ii) a bolus signal using a bolus signal profile, the distance path and total distance traveled, wherein a current time interval is incremented by a defined time step.

In accordance with other various embodiments, a method for Magnetic Resonance Angiography (MRA) is provided. The method includes obtaining Magnetic Resonance (MR) velocity data, determining a distance map for one or more vessels to define a distance path and integrating on a pixel-by-pixel basis a distance traveled of a dynamic virtual bolus using the MR velocity data over a plurality of image fields-of-view. The method further includes translating the integrated distance traveled to a bolus signal using a bolus model.

In accordance with yet other various embodiments, a Magnetic Resonance Imaging (MRI) system is provided that includes an imaging portion configured to acquire Magnetic Resonance (MR) velocity data. The MRI system also includes a processing portion having a virtual bolus Magnetic Resonance Angiography (MRA) module configured to determine a distance map for one or more vessels to define a distance path and calculate, using the MR velocity data, at a plurality of time intervals and for a plurality of pixels (i) a distance traveled during a current time interval as a current distance traveled, wherein a total distance traveled is incremented by the current distance traveled and (ii) a bolus signal using a bolus signal profile, the distance path and total distance traveled, wherein a current time interval is incremented by a defined time step.

BRIEF DESCRIPTION OF THE DRAWINGS

FIG. 2 illustrates velocity images used in various embodiments.

FIG. 3 illustrates a vessel network on which MRA in accordance with various embodiments may be applied.

DETAILED DESCRIPTION

Figure 1:
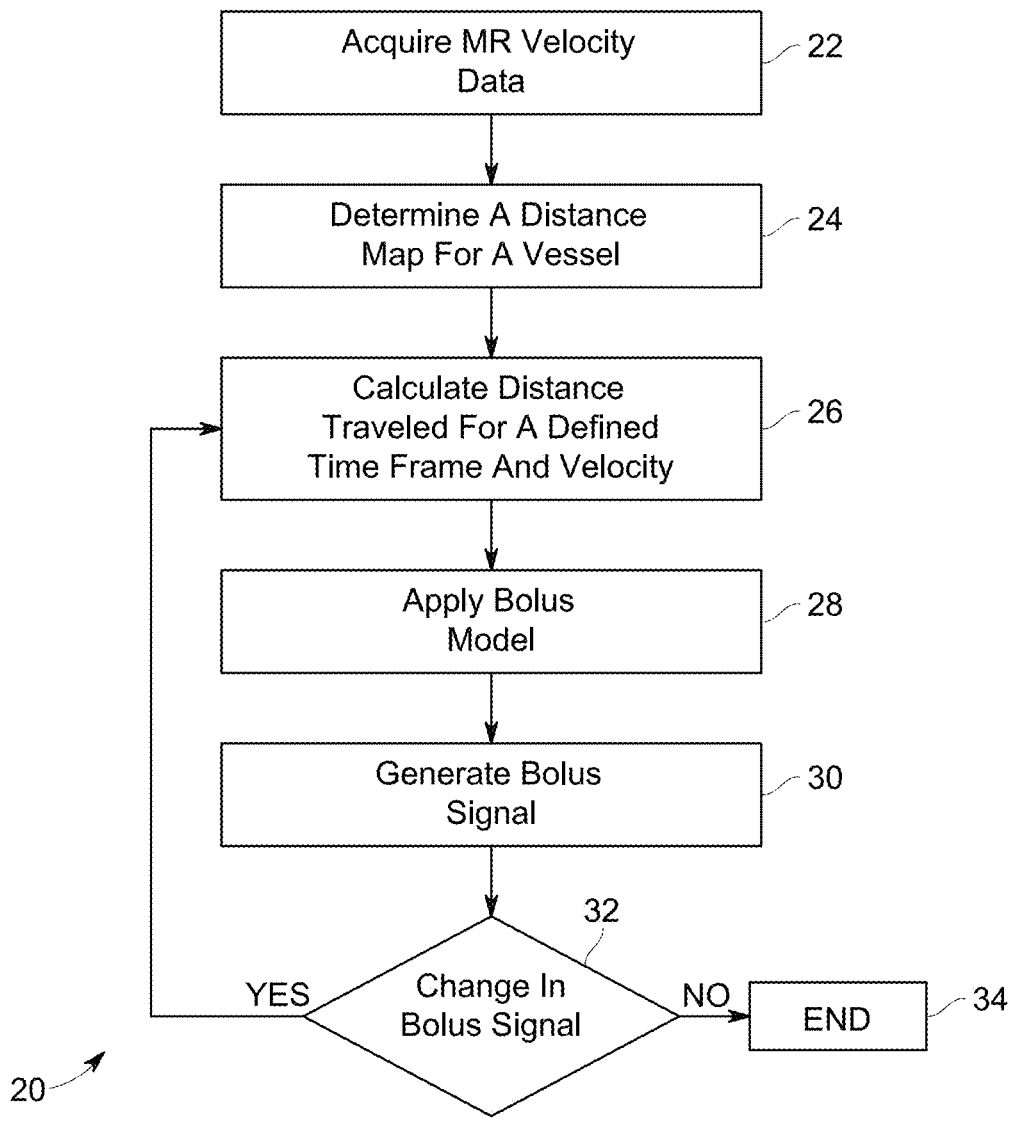
FIG. 1 is a flowchart of a method for performing Magnetic Resonance Angiography (MRA) in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware. Thus, for example, one or more of the functional blocks may be implemented in a single piece of hardware or multiple pieces of hardware. It should be understood that the various embodiments are not limited to the arrangements and instrumentality shown in the drawings. Additionally, the system blocks in the various figures or the steps of the methods may be rearranged or reconfigured.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide for Magnetic Resonance Angiography (MRA), and in particular Dynamic Virtual Bolus MRA (DVB-MRA). By practicing various embodiments, MRA may be performed without the use of an injected contrast agent and that may result in higher temporal resolution. In contrast to using contrast-enhanced MRA (CE-MRA), the entire image in various embodiments in not acquired over the period of preferential vascular enhancement (i.e. duration of the bolus transit in the target vessels), which typically is several tens of seconds, such that the true temporal resolution of the CE-MRA images is of the order of several seconds or tens of seconds or more.

One or more embodiments use a dynamic virtual bolus that allows tracing or tracking of the passage of the "virtual" bolus at the temporal resolution of the phase-contrast acquisition sequence. This temporal resolution in various embodiments is of the order of 20-200 milliseconds (ms), depending on the acquisition parameters. Hence, the passage of the "virtual" bolus can be visualized at a higher temporal resolution.

Various embodiments provide a temporal resolution that allows visualization of the pulsatility of blood flow. For example, one of the DVB-MRA methods described herein has a sufficiently high temporal resolution, such as at least 1-2 orders of magnitude higher than CE-MRA, such that that vessel pulsatility can be visualized. The ability to visualize pulsatility gives DVB-MRA a capability similar to X-ray contrast angiography where the contrast bolus passage is visualized in real-time. However, various embodiments do not use ionizing radiation, invasive percutaneous intravascular catheter placement and/or iodinated contrast media. Using the visualized vessel pulsatility or a lack thereof can provide an indication of diseased vasculature. Thus, various embodiments may provide diagnostic information in addition to visualizing the vasculature without the use of an exogenous contrast media.

More particularly, in various embodiments, velocity data acquired with Magnetic Resonance Imaging (MRI) in a cardiac-triggered cine acquisition is integrated across time and image space to produce dynamic images, for example a dynamic movie that extends beyond the duration of a single cardiac cycle. The dynamic movie reflects the time passage of a virtual bolus of blood vessels as captured by the velocity-encoded MRI acquisition. Also, the time passage of the dynamic movie can extend beyond that of a single cardiac cycle. Thus, various embodiments provide a phase-contrast (PC) cine MRA with high temporal resolution (e.g., about 20 frames per heartbeat). It should be noted that the cardiac-triggered PC-cine acquisition in various embodiments does not have to depict blood flow over a particular representative cardiac cycle (e.g., from one cardiac R-wave trigger to the next cardiac R-wave trigger). In some embodiments, cardiac triggering can be realized, for example, using either electrocardiogram (ECG) signals or peripheral pulse gating signals.

In various embodiments described herein a method is provided for using the information in a PC-cine acquisition to track the passage of a plurality of voxels (containing moving blood) through the vasculature over time. The resulting time frames extend well beyond that of a single cardiac cycle. Specifically, in tracing or tracking the passage of the "virtual" bolus, the velocity and direction of the blood flow at a specific time point in the cardiac cycle is used to compute the distance traveled and the location of the next section of the vasculature. At the new position, the velocity and direction of the blood flow to the next position is computed using the PC-cine information at the next time interval in the cardiac cycle. As the process is repeated to trace or track the passage of the "virtual" bolus, this overall time for the blood to transit through the entire vasculature of interest may extend well beyond the time for a single cardiac cycle.

More particularly, various embodiments provide a method 20 as shown in FIG. 1 for performing MRA. The method 20 generally provides virtual bolus MRA as described in more detail, such as for pulsatile angiography of peripheral arteries. The method 20 allows for converting a cine PC velocity image into continuous time series images that reflects the fluid bolus along the vessels of interest.

The method 20 includes acquiring MR velocity data at 22. For example, in various embodiments cine (cardiac phase) images with PC MRI are acquired to obtain velocity data in one or more encoded directions. Thus, for example, the input to the method 20 may include a cardiac-phase series of velocity images 40 as shown in FIG. 2. The images 40 may be acquired using any suitable MR imaging method. The images 40 are a series of images representing velocity (e.g., flow of blood), wherein white regions represent higher velocity and darker regions represent lower velocities. In one embodiment, the series of images 40 represents a twenty-image cardiac cycle that allows a determination of the velocities for each of a plurality of time frames. As can be seen, the images 40 may be synchronized to an electrocardiogram (ECG) signal 42. It should be noted that the patient's pulse may also be used as the synchronizing trigger signal.

The series of images 40 may correspond to MR data in one-dimension or multiple dimensions. For example, in one embodiment, one-directional (1D) velocity-encoding is used and assumes that the velocities in the vessels are dominated by flow in that encoding direction. However, in other embodiments, data from multiple encoding directions may be used. It should be noted that the pulsatility in the peripheral vasculature can be used to distinguish arterial signals from venous signals, in addition to the directionality of the blood flow direction. It should be noted that in various embodiments, conversely, the lack of pulsatility in an artery suggests the presence of proximal or upstream arterial disease.

Figure 4:
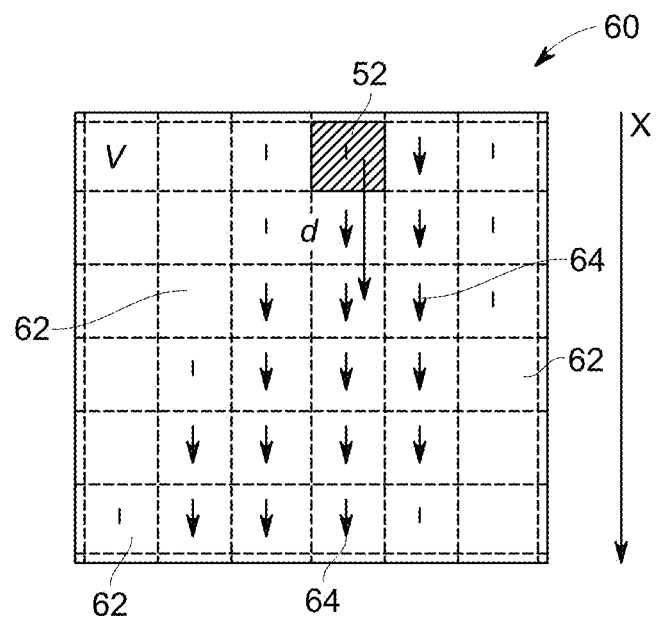
FIG. 4 is a diagram of distance map in accordance with an embodiment.

The method then includes determining a distance map for one or more vessels at 24. For example, a distance map may be determined for a vessel network 50 as shown in FIG. 3, illustrating a simple vessel network for ease of illustration. In particular, a distance map is determined between the source of the bolus 52 and ending at the terminations 54 of the vessel tributaries 56. One example of a distance map 60 is shown in FIG. 4. The distance map 60 may be used to define the general direction of passage of the bolus 52 (represented by the shaded box) along a distance X. In the case of 1D velocity encoding, the distance map value, X, of an image pixel 62 is defined by the coordinate of the pixel in the direction of the velocity-encoding, wherein X increases from the source to the termination of the bolus (illustrated from the top to the bottom of the distance map 60).

The distance map 60 shows the velocity (v) integral represented by the vector arrows 64, such that the longer the vector arrow 64 the higher the velocity. It should be noted that in the distance map 60, the distance d represents the distance traveled at the current time interval, while the distance map value is X. In one embodiment, the distance map 60 may correspond to the distance from the top to the bottom of the legs of a person, such that the bolus 52 starts at the top of the distance map 60 and ends at the bottom of the distance map 60 as viewed in FIG. 4. It should be noted that the assumed starting point or source for the bolus may also be at any other point or area of interest, such as not within the legs of the patient, or somewhere between the source and the termination of the bolus.

Referring again to the method 20, using the distance map 60, a distance traveled for the bolus over a defined time frame and velocity is calculated at 26. In various embodiments, steps 26, 28 and 30 of the method 20 are performed at each time point and for each vascular pixel 62. More particularly, at 26, the distance (d) traveled during the current time interval is computed as the product between the velocity v and the time interval Δt as shown in FIG. 4. Thus, in various embodiments, for the current discrete time frame t and the pixel n, $d_{t,n}=v_{t,n}*\Delta t$. It should be noted that in various embodiments, the distance traveled is valid only if the MR velocity data is within one or more boundaries of the vasculature structure.

Then, the total distance traveled (D) is incremented by the current distance traveled. Accordingly, the total distance traveled for the time frame t may be defined as $D_{t,n}=D_{t-1,n}+d_{t,n}$, where t−1 is the previous time frame. In other words, the current distance traveled (d) may be added to a counter that accumulates the total distance traveled (D). In various embodiments, beginning at the source of the bolus 52 (as shown, for example in FIG. 3), for each time step, which may be a defined time frame, the distance traveled is calculated based on the velocity at the source. Thus, in various embodiments, the position of the bolus is not needed and the accumulation of distance versus the distance map is used.

Figure 5:
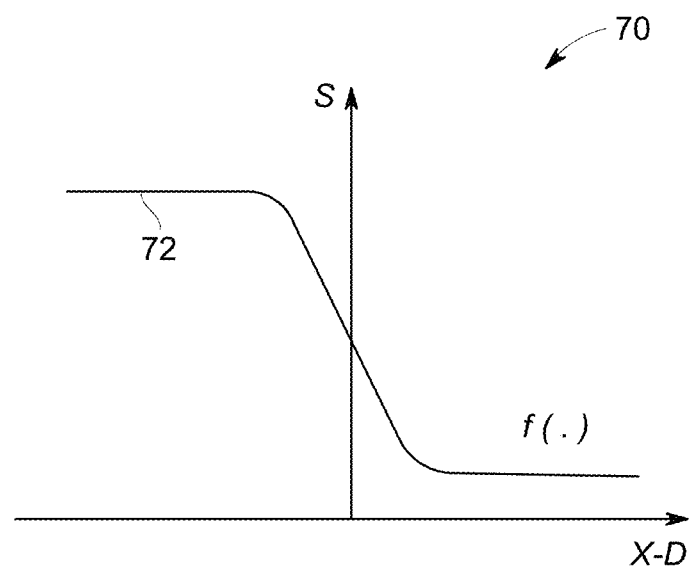
FIG. 5 is a graph of a bolus model in accordance with an embodiment.

Thereafter, a bolus model is applied at 28. An exemplary bolus model 70 is illustrated in FIG. 5 by the curve 72. However, it should be appreciated that different curves and/or different bolus models may be used and the illustrated bolus model 70 is simply one non-limiting example. Accordingly, in various embodiments, X and D are used to obtain or generate a bolus signal (S) at 30 (X-D) using an assumed bolus signal profile represented by the curve 72 in one embodiment. For example, in one embodiment, the assumed bolus model 70, for the bolus signal S, is applied as follows: s=f(X,D).

In the bolus model 70, the horizontal axis represents X-D and the vertical access represents the amplitude or magnitude of the bolus signal S. In this example, the signal is high (value of 1) when the bolus arrives at a given image pixel, otherwise the signal is 0 if the signal has not arrived. In other words, if D is greater than X, the signal is high and if D is less than X then no signal has arrived. The curve 72 represents a continuum of the bolus signal S between 0 and 1 (or any non-zero value). Thus, the curve 72 is one embodiment is shaped to mimic the flow of blood (e.g., the flow of a contrast agent in blood).

It should be noted that a valid arrival position is one that is within the vasculature structure as determined from the magnitude images of the phase-contrast cine acquisition. This is because blood flow cannot extend beyond the confines of a blood vessel.

The time step or time is incremented with steps 26, 28 and 30 iteratively performed if the bolus signal has changed or changed by more than a predetermined amount from the previous iteration as determined at 32. Thus, steps 26, 28 and 30 are repeated (providing an integration operation) until there are no changes to the overall bolus signal S or the change is within a defined threshold or level. If there is no overall change to the bolus signal or if the change is within the defined threshold or level, then the method 20 ends at 34, and for example, an MRA image may be generated and displayed. It should be noted that different outputs for display may be generated. For example, a movie of S shown with maximum-intensity-projection (MIP) processing may be provided with the bolus signal colorized and displayed with anatomical images. Another example of an output is the arrival time of the bolus obtained directly from the dynamic information and which may be displayed with time-of-arrival maps. In various embodiments, a sequence of images at different time points may be displayed that depicts the filling of a vessel similar to that of visualizing the passage of an exogenous contrast agent, as a function of time.

Figure 7:
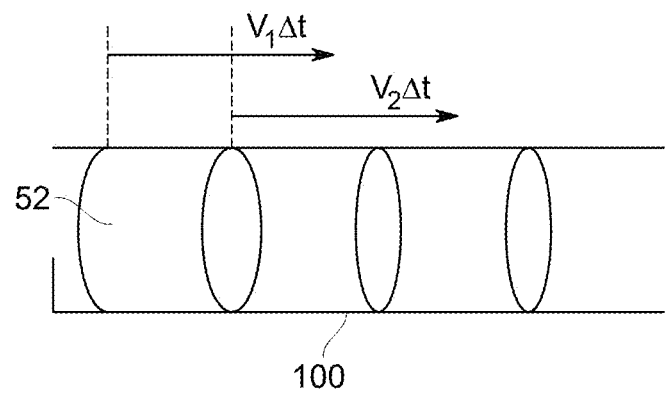
FIG. 7 is a diagram illustrating velocity data in accordance with various embodiments.

Thus, various embodiments provide a pixel-by-pixel basis of showing blood flow. In particular, a pixel-by-pixel integration, which includes the application of a bolus model is used such that the distance traveled is translated into a bolus signal using the bolus model. For example, as shown in FIG. 7, velocity data may be displayed as a virtual bolus passage, such as the virtual passage of a bolus 52 through a vessel 100. The velocity data may be used, for example, to evaluate distensibility, discern right/left differential flow and/or for contrast dose management (that is, to determine bolus arrival times).

Various embodiments, thus, allow the visualization of the passage of a "virtual" contrast bolus through the vasculature, selectively imaging arteries or veins or both. Various embodiments provide visualization of long segments of the vasculature and are not limited by an imaging field-of-view. Various embodiments do not use exogenous contrast agents or media. The resulting images in some embodiments are similar to that obtained in a contrast-enhanced run-off study that seeks to follow or chase the passage of an injected contrast agent bolus. In a run-off study, an image data set is first acquired within one field-of-view. Subsequently, the patient table is advanced to the next image field-of-view, typically representing the next "station" or segment of the peripheral vasculature, as quickly as possible to avoid venous signal contamination. Venous contamination is acquiring images when the contrast agent bolus has transited the vasculature and is now present in the venous vasculature. Venous contamination is not ideal as the resulting images will contain signals from both arteries and veins, a situation that can confound accurate diagnosis of arterial or venous disease.

However, it should be noted that various embodiments provide methods that are compatible with or without contrast agents, wherein the presence of contrast agent or media may be provided to increase the image signal-to-noise ratio in phase-contrast acquisition pulse sequences. Also, in various embodiments, there is no time restriction for the image acquisition time at a single scan location or image field-of-view as there is no passage of contrast agent or media and no possibility for venous contamination. Moreover, with no time restriction, higher spatial resolution images may be acquired or the number of signal averages may be increased to improve the overall image signal-to-noise ratio. Furthermore, various embodiments are applicable after administration of a low dose (e.g. less than 0.1 mmol/kg) or high dose (e.g. 0.3 mmol/kg) of a Gd-chelate contrast agent.

It further should be noted that various embodiments may also be used after a contrast agent or media has been administered to the patient. The presence of contrast agent and media in the blood even at several minutes after the initial bolus administration will still have an effect of reducing the T1 relaxation time of blood, improving the image signal-to-noise ratio. Thus, various embodiments can either visualize the vasculature without contrast media or allow the visualization of the vasculature after the administration of contrast media (for a purpose other than enhancing the vasculature). An example of the latter may be an initial contrast administration to the patient to rule out an enhancing tumor but also allowing the improved visualization of a specific vascular area without having to administer a second contrast bolus.

Visualization of a "virtual" bolus through the vasculature in accordance with carious embodiments may be used that takes several seconds to tens of seconds. Various embodiments "follow" the passage of the "virtual" bolus by computing the distance and direction traveled in a specified time interval. At the new position, the distance and direction traveled from that location is then computed. The process continues until the logical end of the vasculature is reached. As the passage of the "virtual" bolus is traced, the pixels in the image representing the vasculature may be appropriately high-lighted for visualization.

Figure 6:
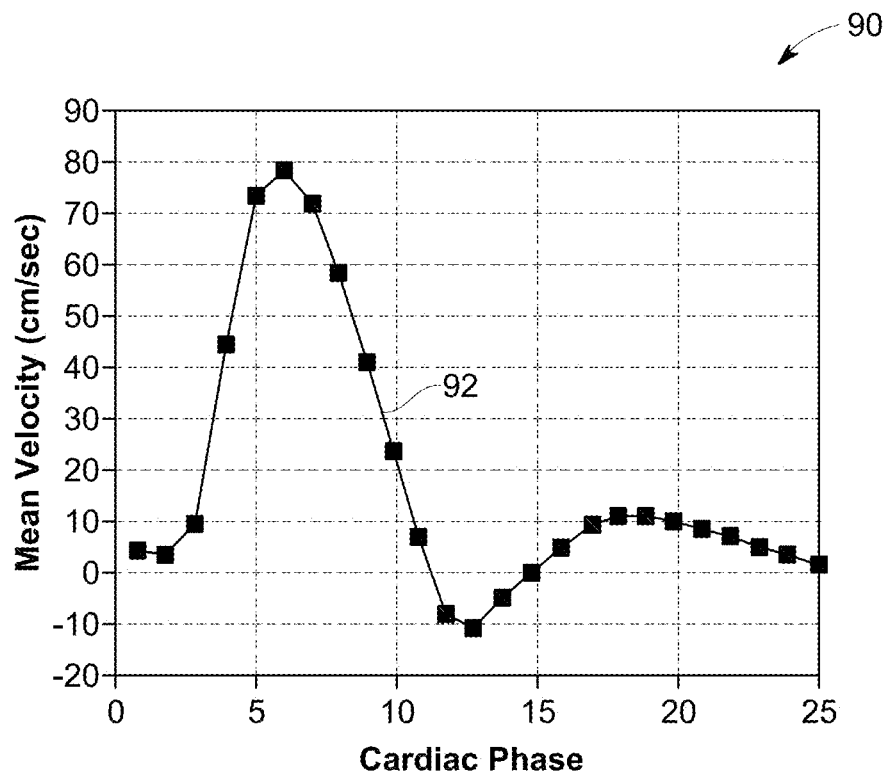
FIG. 6 is a diagram of a velocity-time waveform that may be used in accordance with various embodiments.

It should be noted that variations and modifications are contemplated. For example, blood vessel classification or segmentation (e.g., to detect one or more arteries or veins or one or more sets of vessels) in accordance with some embodiments may be obtained a priori, or from the velocity data. For example, an assumed arterial velocity-time waveform 90 as shown in FIG. 6 may be used to detect arteries, such as by using a match-filtering process. The arterial velocity-time waveform 90 is defined by a curve 92 representing the mean velocity over a cardiac phase. It also should be noted that the segmentation or determination of the vessel pixels may be derived, for example, from the same MR velocity data or from another data set.

Additionally, regional selectivity of velocities may be provided to account for branching vessels and occlusions. For example, the added criteria of bolus signal from the previous time interval, and the radial distance to the evaluated pixel can both be used, namely the X value can be multi-dimensional and can vary with time.

Additionally, different bolus signal models may be used instead of the simple bolus profile 70, which is an error function of (X-D) that has normalized values between 0 and 1, subject to a width, w. For example, complex models may incorporate the effects of diffusion over time.

Accordingly, various pre-processing steps may be applied to the cine-PC-MRI data, including correction for background phase due to eddy currents, segmentation of the blood vessels, regional-based processing of velocities and distances traveled, as well as choice of the bolus signal profile, and various ways to display the DV-bolus images.

Figure 8:
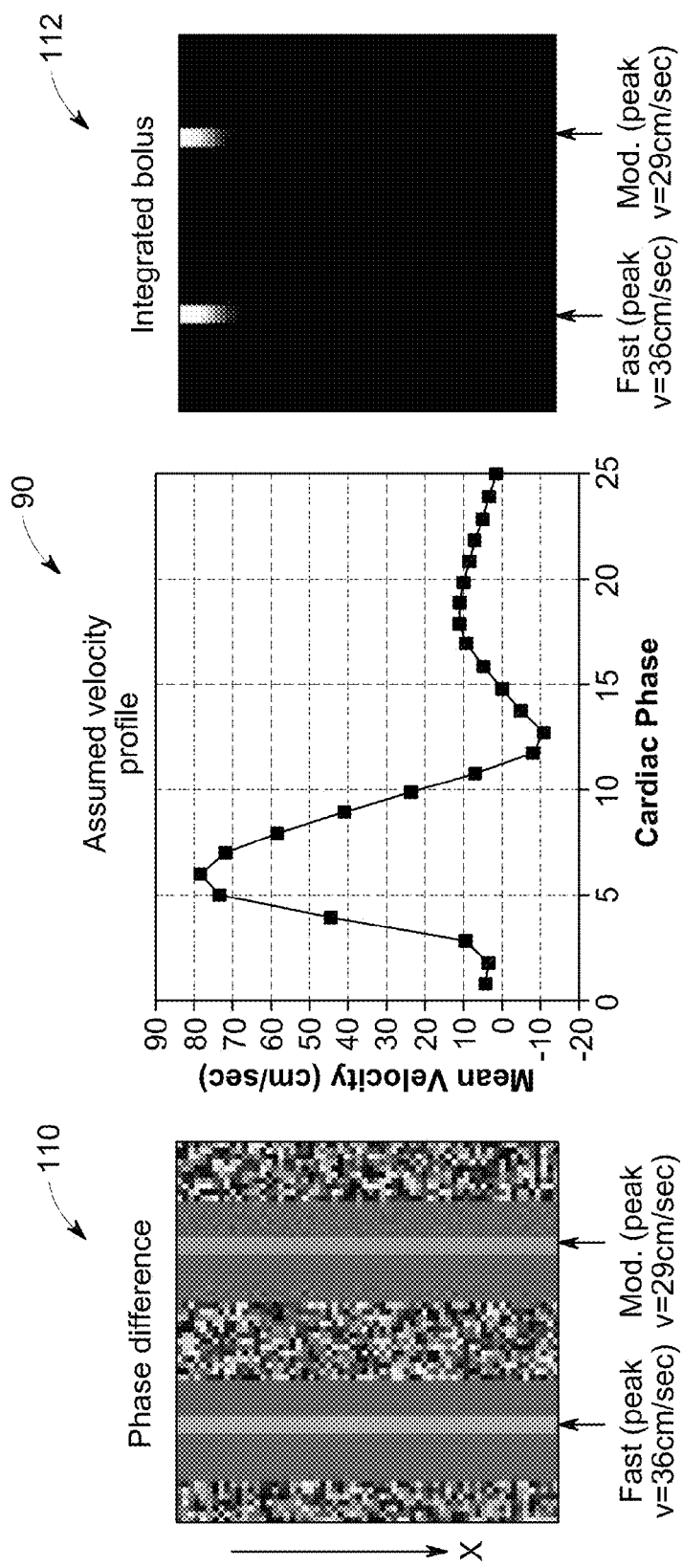
FIG. 8 is a diagram illustrating MRA in accordance with various embodiments.

Thus, as shown in FIG. 8, using a phase difference illustrated by the image 110 and the profile 90, an integrated bolus image 112 may be generated in accordance with various embodiments. Various embodiments provide DVB-MRA wherein velocity data from PC-MRI is integrated over time to determine the distance traveled and the distance traveled is processed with respect to a fixed distance path. An assumed bolus signal profile is then applied, which is a function of the distance traveled and the distance path. The illustration in FIG. 8 corresponds to a cardiac duration of 1000 milliseconds (ms) having 20 phases, a same velocity profile for all pixels and a time resolution of 4 phases. It should be noted that one path per vessel is assumed.

Figure 9:
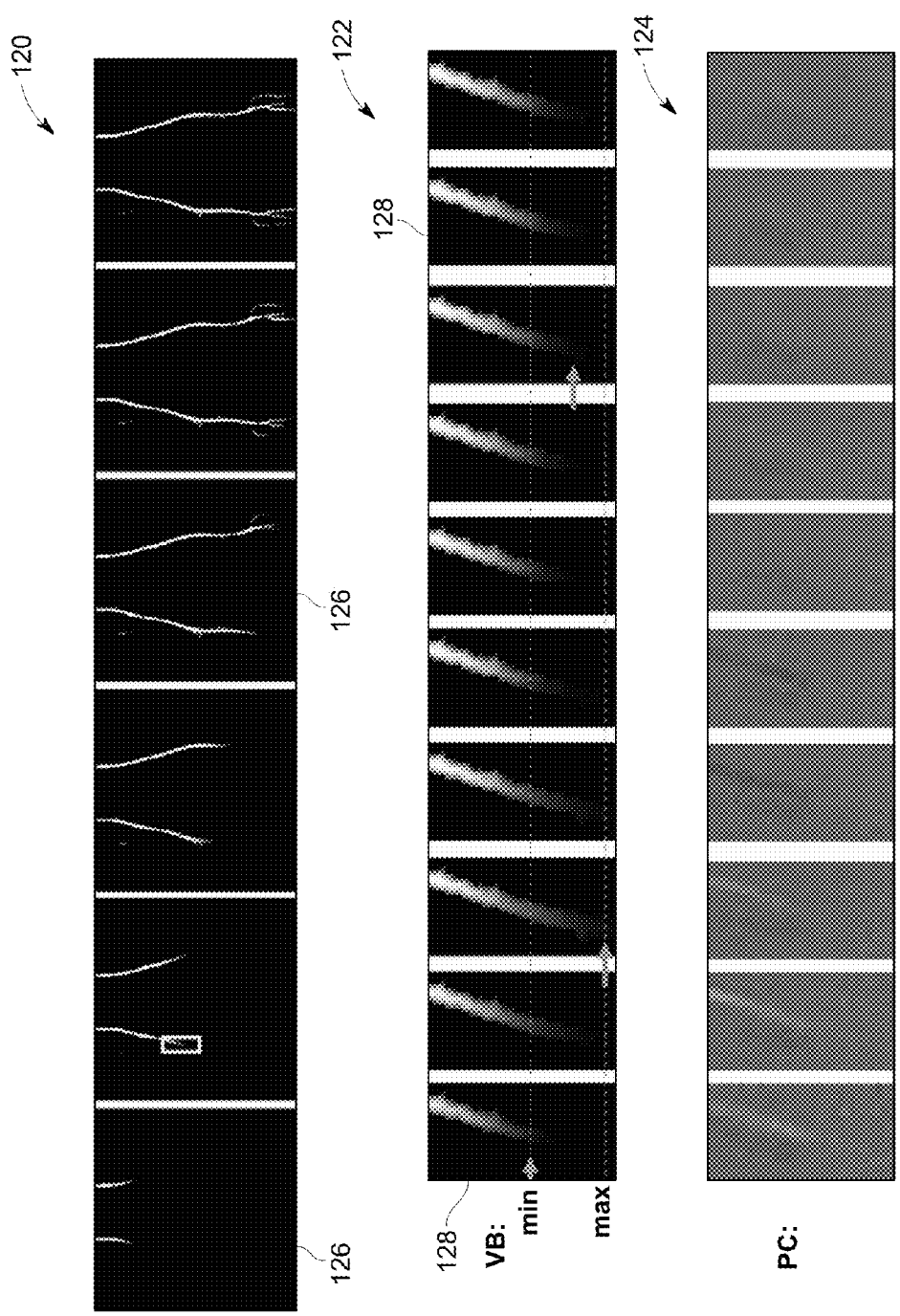
FIG. 9 is another diagram illustrating MRA in accordance with various embodiments.

As another example, FIG. 9 shows the output of various embodiments providing the results of the virtual bolus process. The images represent images from the thigh to the knees of a person. The image sequence 120 represents a virtual bolus sequence over a longer period of time, illustrated as 2.2 seconds (sec) between each MIP frame 126. The image sequence 122 represents a virtual bolus sequence over a shorter period of time, illustrated as 71 ms between each MIP frame 128. Additionally, PC images 124 may be displayed in combination (e.g., on the same screen or separately) with the image sequence 120 or 122. The image sequences 120 and 122 represent two-dimensional cine PC with velocity encoding in the superior-inferior (vertical in the figure) direction over 20 phases with 4 acquisitions per frame.

The images of FIG. 9 provide a representative data set that shows the passage of a "virtual" contrast bolus over time at a temporal resolution that in various embodiments is greater, and in some instances significantly greater, than using an exogenous contrast agent with a non DVB-MRA image acquisition method. One or more of the DVB-MRA methods described herein are able to visualize the true pulsatility of the blood flow in the peripheral vessels and also shows the differential filling between the left and right arterial trees of the peripheral vasculature. By being able to demonstrate the pulsatility of the peripheral vasculature in addition to depicting the dynamic nature of blood flow, other diagnostic information is obtained, such as the distensibility of the blood vessels.

Figure 10:
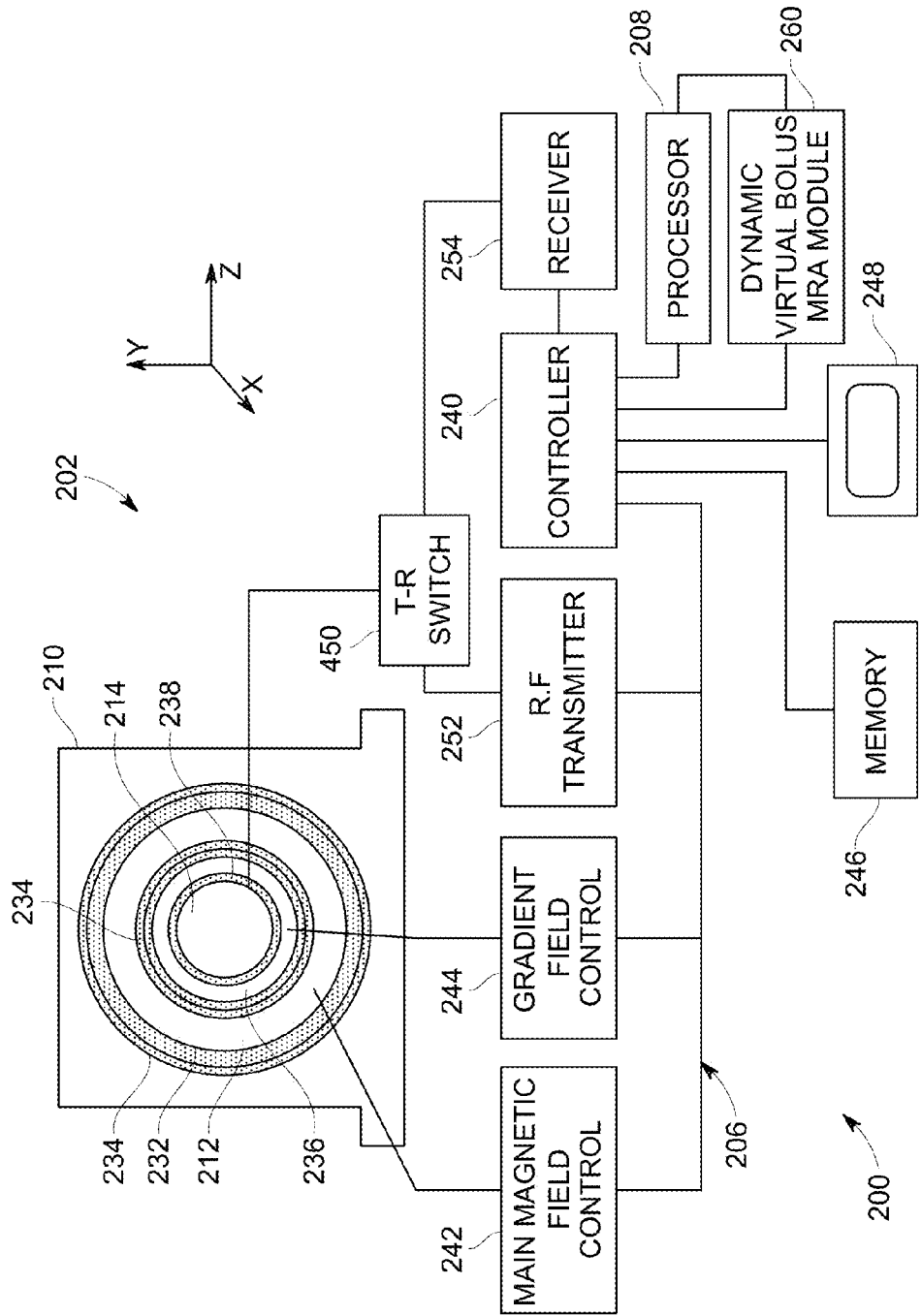
FIG. 10 is a schematic block diagram illustrating a Magnetic Resonance Imaging (MRI) system in accordance with various embodiments.

Various embodiments may be implemented with different MRI systems. For example, the MRI system 200 shown in FIG. 10 that generally includes within a gantry 210, a magnet 212, for example, a superconducting magnet formed from coils, which may be supported on a magnet coil support structure. A helium vessel 232 (also referred to as a cryostat) surrounds the magnet 212 and may be filled with liquid helium. The liquid helium may be used to cool a coldhead sleeve and/or a thermal shield.

Thermal insulation 234 is provided surrounding the outer surface of the helium vessel 232 and the inner surface of the magnet 212. A plurality of magnetic gradient coils 236 are provided inside the superconducting magnet 212 and an RF transmit coil 238 is provided within the plurality of magnetic gradient coils 236.

In some embodiments, the RF transmit coil 238 may be replaced with a transmit and receive coil. The components within the gantry 210 generally form the imaging portion 202. It should be noted that although the magnet 212 is a cylindrical shape, other shapes of magnets can be used.

The processing portion 206 generally includes the controller 240, a main magnetic field control 242, a gradient field control 244, a memory 246, a display device 248, a transmit-receive (T-R) switch 250, an RF transmitter 252 and a receiver 254.

In operation, a body of an object, such as a patient or a phantom to be imaged, is placed in a bore 214 on a suitable support, for example, a patient table. The magnet 212 produces a uniform and static main magnetic field Bo across the bore 214. The strength of the electromagnetic field in the bore 214 and correspondingly in the patient, is controlled by the controller 240 via the main magnetic field control 242, which also controls a supply of energizing current to the superconducting magnet 212.

The magnetic gradient coils 236, which include one or more gradient coil elements, are provided so that a magnetic gradient can be imposed on the magnetic field Bo in the bore 212 within the magnet 212 in any one or more of three orthogonal directions x, y, and z. The magnetic gradient coils 236 are energized by the gradient field control 244 and are also controlled by the controller 240.

The RF transmit coil 238, which may include a plurality of coils, is arranged to transmit RF magnetic pulses and/or optionally simultaneously detect MR signals from the patient if receive coil elements are not. If a receive coil is provided, the coil may be of any type or configuration, for example, a separate receive surface coil, such as a knee coil. The receive surface coil may be an array of RF coils provided within the RF transmit coil 238.

The RF transmit coil 238 and the receive surface coil are selectably interconnected to one of the RF transmitter 252 or receiver 254, respectively, by the T-R switch 250. The RF transmitter 252 and T-R switch 250 are controlled by the controller 240 such that RF field pulses or signals are generated by the RF transmitter 252 and selectively applied to the patient for excitation of magnetic resonance in the patient. While the RF excitation pulses are being applied to the patient, the T-R switch 250 is also actuated to disconnect the receive surface coil from the receiver 254.

Following application of the RF pulses, the T-R switch 250 is again actuated to disconnect the RF transmit coil 238 from the RF transmitter 252 and to connect the receive surface coil to the receiver 254. The receive surface coil operates to detect or sense the MR signals resulting from the excited nuclei in the patient and communicates the MR signals to the receiver 254. These detected MR signals are in turn communicated to the controller 240. The controller 240 includes a processor (e.g., image reconstruction processor), for example, that controls the processing of the MR signals to produce signals representative of an image of the patient, which may include using a virtual bolus MRA module, such as a dynamic virtual bolus MRA module 260 that performs one or more of the various embodiments as described herein. It should be noted that the virtual bolus MRA module 460 may be implemented in hardware, software, or a combination thereof. Also, the landmark virtual bolus MRA module 460 may be separate for or provided as part of a processor 208.

The processed signals representative of the image are also transmitted to the display device 248 to provide a visual display of the image. Specifically, the MR signals fill or form a k-space that is Fourier transformed to obtain a viewable image. The processed signals representative of the image are then transmitted to the display device 248.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, Reduced Instruction Set Computers (RISC), Application Specific Integrated Circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from the scope thereof. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A non-transitory computer readable storage medium for Magnetic Resonance Angiography (MRA) using a processor, the non-transitory computer readable storage medium including instructions to command the processor to:
   obtain Magnetic Resonance (MR) velocity data;
   determine a distance map for one or more vessels to define a distance path;
   calculate, using the MR velocity data, at a plurality of time intervals and for a plurality of pixels (i) a distance traveled during a current time interval as a current distance traveled, wherein a total distance traveled is incremented by the current distance traveled and (ii) a bolus signal using a bolus signal profile, the distance path and total distance traveled, wherein a current time interval is incremented by a defined time step; and display a sequence of images at different time points that depict the filling of a vessel as a function of time based on the bolus signal.

2. The non-transitory computer readable storage medium of claim 1, wherein the instructions command the processor to iteratively perform the calculation until a change in the calculated bolus signal is within a defined threshold.

3. The non-transitory computer readable storage medium of claim 1, wherein the instructions command the processor to acquire cine images with MR velocity data in one or more encoded directions.

4. The non-transitory computer readable storage medium of claim 1, wherein the instructions command the processor to determine the distance map in a vessel network from an assumed source of the bolus to one or more terminations of vessel tributaries in the vessel network.

5. The non-transitory computer readable storage medium of claim 1, wherein the bolus signal profile is an assumed profile as a function of the distance traveled and the distance path.

6. The non-transitory computer readable storage medium of claim 1, wherein the instructions command the processor to perform the calculation using an integration on a pixel by pixel basis.

7. The non-transitory computer readable storage medium of claim 1, wherein the instructions command the processor to translate the total distance traveled into the bolus signal using a bolus model.

8. The non-transitory computer readable storage medium of claim 1, wherein the instructions command the processor to determine that the distance traveled is valid only if the MR velocity data is within one or more boundaries of a vasculature structure.

9. A method for Magnetic Resonance Angiography (MRA) comprising:
   obtaining Magnetic Resonance (MR) velocity data;
   determining a distance map for one or more vessels to define a distance path;
   integrating on a pixel-by-pixel basis a distance traveled of a dynamic virtual bolus using the MR velocity data over a plurality of fields-of-view;
   translating the integrated distance traveled to a bolus signal using a bolus model; and
   displaying a sequence of images at different time points that depict the filling of a vessel as a function of time based on the bolus signal.

10. The method of claim 9, wherein the integrating and translating comprises calculating, using the MR velocity data, at a plurality of time intervals and for a plurality of pixels (i) a distance traveled during a current time interval as a current distance traveled, wherein a total distance traveled is incremented by the current distance traveled and (ii) the bolus signal using a bolus signal profile defined by the bolus model, the distance path and total distance traveled, wherein a current time interval is incremented by a defined time step.

11. The method of claim 10, further comprising iteratively performing the calculating until a change in the calculated bolus signal is within a defined threshold.

12. The method of claim 9, wherein the obtaining comprises acquiring cine images with MR velocity data in one or more encoded directions.

13. The method of claim 9, wherein determining the distance map comprises determining the distance map in a vessel network from an assumed source of the bolus to one or more terminations of vessel tributaries in the vessel network.

14. The method of claim 9, wherein the bolus model comprises a bolus signal profile being an assumed profile as a function of the distance traveled and the distance path.

15. A Magnetic Resonance Imaging (MRI) system comprising:
   an imaging portion configured to acquire Magnetic Resonance (MR) velocity data; and
   a processing portion having a dynamic virtual bolus Magnetic Resonance Angiography (MRA) module configured to determine a distance map for one or more vessels to define a distance path and calculate, using the MR velocity data, at a plurality of time intervals and for a plurality of pixels (i) a distance traveled during a current time interval as a current distance traveled, wherein a total distance traveled is incremented by the current distance traveled and (ii) a bolus signal using a bolus signal profile, the distance path and total distance traveled, wherein a current time interval is incremented by a defined time step.

16. The MRI system of claim 15, wherein the dynamic virtual bolus MRA module is configured to iteratively perform the calculating until a change in the calculated bolus signal is within a defined threshold.

17. The MRI system of claim 15, wherein the imaging portion is configured to acquire cine images with MR velocity data in one or more encoded directions.

18. The MRI system of claim 15, wherein the dynamic virtual bolus MRA module is configured to determine the distance map in a vessel network from an assumed source of the bolus to one or more terminations of vessel tributaries in the vessel network.

19. The MRI system of claim 15, wherein the bolus signal profile is an assumed profile as a function of the distance traveled and the distance path.

20. The MRI system of claim 15, wherein the dynamic virtual bolus MRA module is configured to perform the calculating using an integration on a pixel by pixel basis.

21. The MRI system of claim 15, wherein the dynamic virtual bolus MRA module is configured to translate the total distance traveled into the bolus signal using a bolus model.

22. The MRI system of claim 15, wherein the plurality of pixels is vasculature pixels identified from the MR velocity data.

23. The MRI system of claim 15, wherein the plurality of pixels are vasculature pixels identified from an image data source separate from the MR velocity data.

24. The MRI system of claim 15, wherein the dynamic virtual bolus MRA module is configured to perform the determination and calculation after an injection of a contrast agent for contrast-enhanced MRA.

* * * * *